United States Patent
Aldrich

(10) Patent No.: US 6,463,332 B1
(45) Date of Patent: Oct. 8, 2002

(54) METHOD AND SYSTEM FOR PERICARDIAL ENHANCEMENT

(75) Inventor: William N. Aldrich, Los Altos, CA (US)

(73) Assignee: Core Medical, Inc., Sunnyvale, CA (US)

(*) Notice: Subject to any disclaimer, the term of this patent is extended or adjusted under 35 U.S.C. 154(b) by 173 days.

(21) Appl. No.: 09/661,987

(22) Filed: Sep. 14, 2000

Related U.S. Application Data

(60) Provisional application No. 60/154,430, filed on Sep. 17, 1999.

(51) Int. Cl.[7] ................................................ A61F 2/00
(52) U.S. Cl. ........................ 607/101; 607/100; 607/105
(58) Field of Search .............................. 607/96, 98, 99, 607/100, 101, 102, 104, 113, 115, 120

(56) References Cited

U.S. PATENT DOCUMENTS

| | | | |
|---|---|---|---|
| 4,536,893 A | 8/1985 | Parravicini | |
| 5,131,905 A | 7/1992 | Grooters | |
| 5,273,518 A | 12/1993 | Lee et al. | |
| 5,385,528 A | 1/1995 | Wilk | |
| 5,533,958 A | 7/1996 | Wilk | |
| 5,603,337 A | 2/1997 | Jarvik | |
| 5,702,343 A | 12/1997 | Alferness | |
| 5,713,954 A | 2/1998 | Rosenberg et al. | |
| 5,785,705 A | 7/1998 | Baker | |
| 5,800,334 A | 9/1998 | Wilk | |
| 5,800,528 A | 9/1998 | Lederman et al. | |
| 6,206,004 B1 * | 3/2001 | Schmidt et al. | 128/898 |
| 6,231,518 B1 * | 5/2001 | Grabek et al. | 600/508 |

\* cited by examiner

*Primary Examiner*—Roy D. Gibson
(74) *Attorney, Agent, or Firm*—Lyon & Lyon LLP

(57) ABSTRACT

The invention modifies the pericardium to treat patients suffering from or at risk of heart failure of the type wherein constraining forces of the pericardium around the heart are inadequate to prevent remodeling of the heart. The pericardium is enhanced by restoring, increasing, or improving its ability to restrain the heart and prevent dilation of the chambers of the heart. Methods and apparatus are provided for stiffening, strengthening, tightening, reshaping, and/or shrinking the pericardium to enhance the restraining and supporting capability of the pericardium around the heart. Specific embodiments enhance the pericardium by heating the pericardial tissue using radiofrequency energy and the like, treating the pericardium with a chemical such as glutaraldehyde, plicating the pericardium, or some combination of the above.

45 Claims, 7 Drawing Sheets

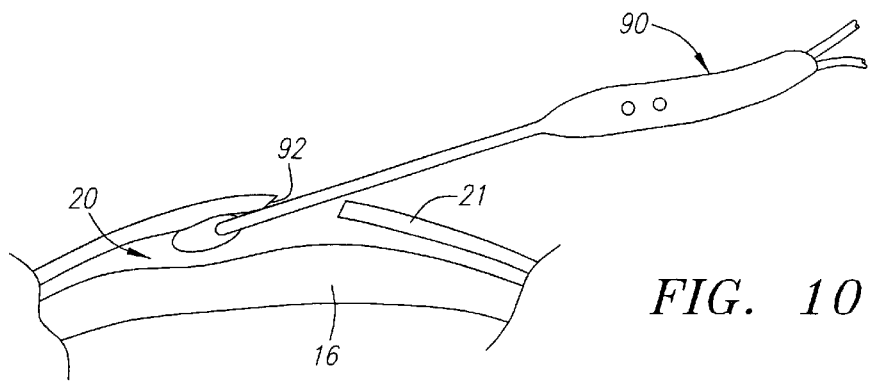
FIG. 10
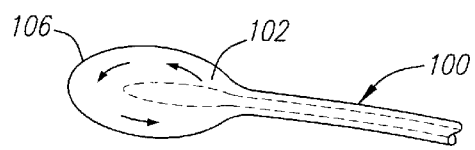
FIG. 11
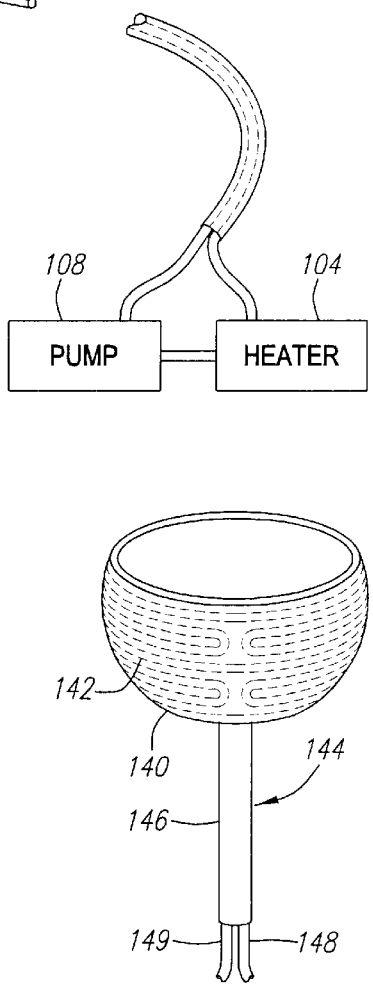
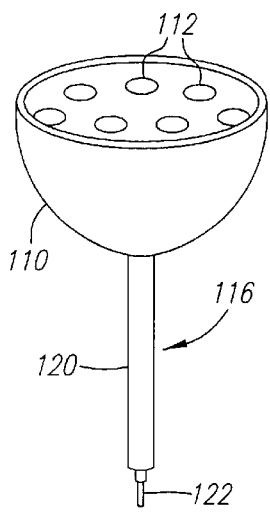
FIG. 12A
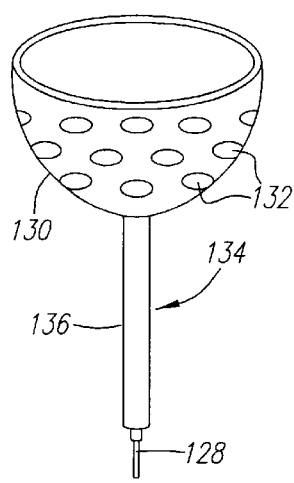
FIG. 12B
FIG. 13

METHOD AND SYSTEM FOR PERICARDIAL ENHANCEMENT

This application claims the benefit of U.S. Provisional Application Serial No. 60/154,430, filed on Sep. 17, 1999, the disclosure of which is expressly incorporated herein.

FIELD OF THE INVENTION

The present invention relates generally to pericardial enhancement, and more particularly to methods and systems for modifying the pericardium to reduce or eliminate remodeling of the heart for patients suffering from or at risk of heart failure.

BACKGROUND OF THE INVENTION

A common form of heart disease involves cardiac dilation. Ventricular dilatation, for example, increases the load on the heart and decreases cardiac efficiency, producing symptoms of congestive heart failure. The ventricular walls grow thinner and more vulnerable as a result of ventricular dilatation and associated increase in wall stresses.

Healthy pericardium provides a constraint around the myocardium to prevent dilatation of the chambers of the heart. For patients suffering from or at risk of heart disease, the constraining forces of the pericardium may be inadequate to prevent dilatation of the chambers of the heart. The pericardium may decrease in rigidity and become excessively compliant, or the natural restraining capability of the pericardium may simply be inadequate to overcome the pressure produced by the cardiac dilation.

Cardiac reinforcement devices have been proposed for treating heart dilation. For example, U.S. Pat. No. 5,702,343 discloses a cardiac reinforcement device having a biocompatible jacket to be placed over the epicardial surface of the heart to constrain cardiac expansion. U.S. Pat. No. 5,800,528 discloses a passive girdle to be wrapped around a heart muscle. The girdle is formed of unattached, linked loops designed to conform to the size and shape of the heart and to constrain the dilatation during diastole. U.S. Pat. No. 5,603,337 is directed to cardiomyoplasty in which a skeletal muscle is grafted around the heart. U.S. Pat. No. 4,536,893 discloses a device having expandable pumping chambers for receiving a pumping fluid to compress the myocardial wall.

Other cardiac muscle wraps are disclosed in Eli R. Capouya et al., "Girdling Effect of Nonstimulated Cardiomyoplasty on Left Ventricular Function," 58 Ann. Thorac. Surg. 867–71 (1993); David A. Kass et al., "Reverse Remodeling from Cardiomyoplasty in Human Heart Failure," 91 Circulation 2314–18 (May 1, 1995); Mikhail Vaynblat et al., "Cardiac Binding in Experimental Heart Failure," 60 Ann. Thorac. Surg. 81–85 (1997); and Joong Hwan Oh et al., "The Effects of Prosthetic Cardiac Binding and Adynamic Cardiomyoplasty in a Model of Dilated Cardiomyopathy," 116 J. Thorac. Cardiovasc. Surg. 148–53 (1998).

The use of radio frequency (RF) energy to induce heat in collagen containing tissue to alter collagen in tissue is known. For example, U.S. Pat. No. 5,458,596 discloses an orthopedic apparatus for delivering RF energy to ligaments, joint capsules and connective tissue. U.S. Pat. No. 5,785,705 discloses an RF ablation apparatus for controlled depth ablation of soft tissue.

Heat-induced shrinkage of collagen tissue has been used for various treatments in the heart. For example, PCT Publication No. WO 98/26738 discloses treating myocardial infarction by selectively heating the infarct scar. U.S. Pat. No. 5,928,224 discloses using heat and/or applying pressure to treat infected or damaged heart valve tissue. Other applications of heat-induced treatment include shrinking the chordae tendinae (WO 98/35638), closing or abrading the patent foramen ovale (WO 99/18871, WO 99/18870, WO 99/18862, U.S. Pat. No. 5,919,200), modifying the collagen fibers of the vein (WO 98/32367), and closing the ductus arteriosus (U.S. Pat. No. 5,827,268).

SUMMARY OF THE INVENTION

The present invention is generally directed to methods and systems for treating patients suffering from or at risk of heart failure. The invention modifies the pericardium to treat heart failure of the type wherein constraining forces of the pericardium on the heart are inadequate to prevent remodeling involving geometric alteration of the heart. The pericardium is enhanced by restoring, increasing, or improving its ability to restrain the heart and prevent dilation of the chambers of the heart. Specific embodiments of the invention cause stiffening, strengthening, tightening, reshaping, and/or shrinking of the pericardium to enhance the restraining and supporting capability of the pericardium around the heart.

The pericardium includes collagen-containing connective tissue. Collagen fibers shrink and tighten when elevated in temperature. This molecular response to temperature elevation is believed to be the result of rupture of the collagen stabilizing cross links and immediate contraction of the collagen fibers to about one-third of their original linear dimension. In addition, the caliber of the individual fibers increases greatly, over four fold, without changing the structural integrity of the connective tissue.

An aspect of the present invention is directed to a method for treating patients suffering from or at risk of heart failure of the type involving inhibiting or preventing remodeling of the heart, for example, by placing an elastic or inelastic constraint surrounding at least a part of the heart. The improvement includes modifying the pericardium under conditions to inhibit remodeling of the heart.

In some embodiments, modifying the pericardium includes heating at least a portion of the pericardium under conditions that shrink collagen within the pericardial tissue while retaining tissue viability. The pericardium may be heated in a pattern of spaced-apart lines in a grid. Alternatively, the entire pericardium may be heated. Selective heating may be performed, for example, below the AV groove or in a region overlying the left ventricle.

In a specific embodiment, the pericardium is heated by contacting the pericardial tissue with a probe that applies RF energy to the pericardial tissue. The RF energy may be applied in a monopolar manner or a bipolar manner. The probe may be placed in contact with the pericardial tissue on the outside of the pericardium or from within the pericardial space. When the pericardium is heated from the outside, the fat on the outside of the pericardium is preferably first removed by mechanical abrasion, thermal ablation, suction, chemicals, or the like.

In another embodiment, at least a portion of the pericardium is conductively heated by placing a heating element in contact with or in close proximity to the pericardial tissue and circulating a heated fluid through the heating element. The heating element will preferably contact the entire area to be reinforced.

In another embodiment, the pericardium is modified by applying a chemical to reduce compliance of the pericardium. The chemical may include glutaraldehyde. The chemical may be removed from the patient substantially contemporaneously with the application of the chemical.

In yet another embodiment, modifying the pericardium includes plicating the pericardium, for example, by suturing or clipping.

A target region of the pericardium that is to be modified may be isolated by anchoring a portion of the pericardium surrounding the target region to the myocardium. Suturing or clipping may be employed in anchoring the portion of the pericardium to the myocardium.

If an anastomosis site is present, a ring of the pericardium may be coupled with the myocardium around the anastomosis. The coupling may involve attaching the ring of pericardium to an annular piece of biomedical material and attaching the annular piece of biomedical material to the myocardium around the anastomosis.

Certain embodiments of the invention involve accessing a region of the pericardium for treatment. The pericardium may be accessed, for example, by surgically opening the patient's chest, forming an intercostal incision, or forming a subxiphoid access channel, or transvascularly via the venous system.

The pericardium may be treated while the heart remains beating or when the heart is stopped.

In accordance with another aspect of the invention, a method for treating patients suffering from or at risk of heart failure includes providing a device having a heating member, and placing the heating member in contact with or in close proximity to the pericardium of the heart. Energy is supplied to the heating member to cause heating of the pericardium under conditions and for a time selected to reduce or eliminate remodeling of the heart.

In one embodiment, the heating member includes an electrode and RF energy is applied through the electrode to the pericardium. In another embodiment, the heating member includes a circulation path and a heated fluid is circulated through the circulation path for heating the pericardium.

The device may include a fluid delivery port for introducing a chemical to the pericardium to reduce compliance of the pericardium. The device may further include a suction port for withdrawing the chemical introduced to the pericardium.

In a method for treating patients suffering from or at risk of heart failure of the type involving provision of constraint around the heart wherein constraining forces of the pericardium around the heart are inadequate to prevent remodeling of the heart, another aspect of the invention is directed to an improvement comprising modifying the pericardial tissue of the pericardium in a manner sufficient to inhibit remodeling of the heart while retaining viability of the heart.

In one embodiment, modifying includes introducing a stiffening chemical to stiffen the pericardium.

In another embodiment, modifying includes shrinking at least a portion of the pericardium. Shrinking may include applying thermal energy to the pericardium under conditions that shrink collagen within the pericardial tissue while retaining tissue viability. Shrinking may include tensioning of the pericardium to restrain the heart.

Another aspect of the invention is directed to a device for treating the pericardium. The device includes a heating member configured to be placed in contact with or in close proximity to the pericardium. A source of energy is coupled with the heating member for providing energy to the heating member to cause heating. The heating member includes a fluid delivery port, and a fluid delivery line extends from the fluid delivery port that is configured to be fluidicly coupled with a source of chemical for introducing the chemical through the fluid delivery port to the pericardium. The device may include a suction line extending from a suction port and being configured to be fluidicly coupled with a vacuum source for withdrawing through the suction port the chemical introduced to the pericardium. In a specific embodiment, RF energy is applied through electrodes provided in the heating member to the pericardium to heat the pericardium.

In accordance with another aspect of the invention, a kit is provided for treating patients suffering from or at risk of heart failure. The kit includes a member configured for modifying the pericardium. In specific embodiments, the member for modifying the pericardium may include a heating member for heating at least a portion of the pericardium, a fluid delivery member for delivering a fluid to the pericardium, and/or a plicating member for plicating the pericardium. The kit further includes instructions for use according to any of the methods set forth above. The kit may optionally further include a package for holding at least the member for modifying the pericardium, and usually the instructions for use. Exemplary packages include boxes, trays, pouches, tubes, and the like. In some embodiments, at least a portion of the member for modifying the pericardium will be maintained sterilely within the package. Optionally, devices for accessing the pericardium may be included. Further, optionally, when a fluid delivery member is provided as a member for modifying the pericardium, one or more chemicals may be included for use with the fluid delivery member.

BRIEF DESCRIPTION OF THE DRAWINGS

FIG. 10 is a cross-sectional side view of a heart, illustrating heating of the pericardium from inside the pericardial space;

FIG. 11 is a perspective view of a heating device having a circulation of heated fluid for heating a pericardium;

FIG. 12A is a perspective view of a radiofrequency heating basket for heating a pericardium from the outside the heart;

FIG. 12B is a perspective view of a radiofrequency heating basket for heating a pericardium from within the pericardial space;

FIG. 13 is a perspective view of a heating basket having a circulation of heated fluid for heating a pericardium from within the pericardial space;

DESCRIPTION OF THE SPECIFIC EMBODIMENTS

The present invention is directed to methods and systems for enhancing a pericardium to treat a patient suffering from dilated and non-dilated heart failure, as well as providing prophylactic treatment for patients at risk of heart failure.

Figure 1:
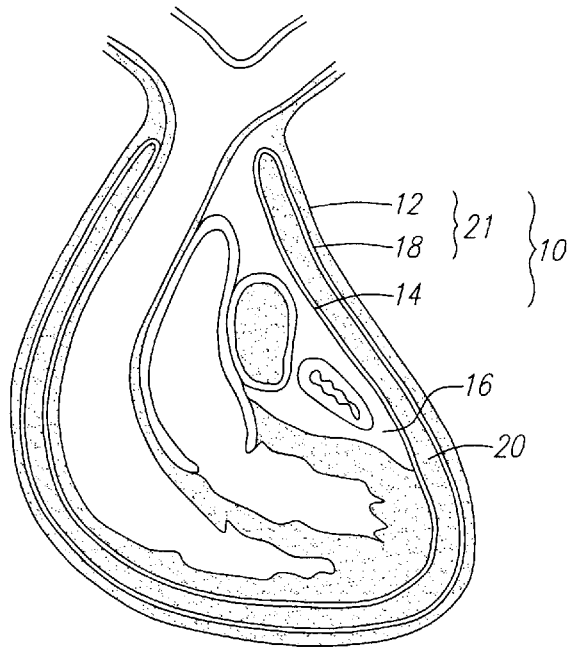
FIG. 1 is a schematic diagram of a heart.

The pericardium functions to prevent dilation of the chambers of the heart, lubricates the surfaces of the heart, and maintains the heart in a fixed geometric position. As shown in FIG. 1, the pericardium 10 consists of the fibrous pericardium 12 and the serosal pericardium 14, 18. The fibrous pericardium 12 is a sac made of tough connective tissue, fully surrounding the heart without being attached to it. The serosal pericardium 14, 18 consists of two sacs of serosal membrane, one inside the other. The inner (visceral) sac 14 adheres to the myocardium 16 and forms its outer covering known as the epicardium, while the outer (parietal) sac 18 lines the internal surface of the fibrous pericardium 12. The two serosal surfaces are separated by a film of fluid filling a space known as the pericardial space or pericardial cavity 20. The fibrous pericardium 12 and parietal sac 18 are sometimes referred to collectively as the pericardial sac 21.

Heart dilation causes a change in the shape of the heart. In ventricular dilation, for example, the normal elliptical shape of the heart with an apical anchor becomes spherical, causing the ventricular wall stresses to increase. As used herein, the term "remodeling" of the heart refers to the geometric alteration of the heart.

The present invention relates to enhancing or modifying the pericardium to reduce or eliminate remodeling of the heart. Pericardial enhancement includes restoring, increasing, or improving the ability of the pericardium, or any combination of the above, to restrain the heart and prevent dilation of the chambers of the heart. For example, pericardial enhancement may include stiffening, strengthening, tightening, shrinking, reshaping, or reducing the compliance of pericardial tissue within the pericardium, or any combination thereof.

One way of enhancing the pericardium involves heating the pericardium. Collagen-containing connective tissue in the pericardium, in particular the fibrous pericardium, may be modified when elevated in temperature. It is believed that the collagen fibers straighten when subjected to heat and, upon cooling, re-entwine or refold around each other, becoming shorter, tighter, thicker, stronger, or stiffer, or some combination of the above. The heat treatment enhances the restraint that the pericardium provides to the heart. Heating the pericardium may result in reshaping and/or tensioning of the pericardium during the treatment or subsequently thereto.

Heat may be applied to or induced in the pericardium by a number of methods. One technique involves conductive heating by contacting a surface or region of the pericardium with a heating medium, such as a heating element or a heated fluid. The pericardium may also be heated using radiant energy, for example, by placing a source of infrared radiation in close proximity to the pericardial tissue. Another technique involves heating the pericardium inductively by directing electromagnetic energy, such as radiofrequency, microwave, or light from either coherent or incoherent sources, into the tissue. Inductive heating may also be applied by passing an electric current through the tissue by means of electrodes inserted into or placed on the surface of the tissue. In addition, energy may be transmitted to the pericardium acoustically such as by ultrasound to induce heating of the tissue.

Some of these techniques, such as conductive heating, require accessing the pericardium, while others, such as acoustic transmission of energy, may be performed noninvasively.

The pericardium may be accessed, for example, through sternotomy, mini or partial sternotomy, thoracotomy, mini-thoracotomy, intercostal incision, or subxiphoid access channel. Access to the pericardium may also be possible by a transvascular approach via the venous system, for example, through the right atrial appendage. The above methods of accessing the pericardium are known in the art, and other minimally invasive techniques may be employed as well.

The pericardium may be treated from the outside or from within the pericardial space. Treating the pericardium from the outside is less invasive because it does not require an incision of the fibrous pericardium and the parietal sac. The pericardial sac may remain closed with the possible exception of a small vent punctured through the pericardial sac for removing some or all of the pericardial fluid before, during, or after treating the pericardium. Treating the pericardium from the inside may be more desirable, however, since the inner surface is more homogenic than the outer surface that is frequently covered in fat and small vessels. When treating the pericardium from the outside using energy or chemicals, the fat on the outer surface may desirably be removed for more effective treatment.

Fat removal may employ mechanical abrasion by scrapping or grinding with a scraper-like device or using a differential cutter that is biased to remove the fat in a manner similar to a Rotoblator™ device without harming the pericardium. The fat may also be removed by thermal ablation, chemically with a fat dissolving compound, or by suction. These techniques may be used individually or in combination.

Figure 2:
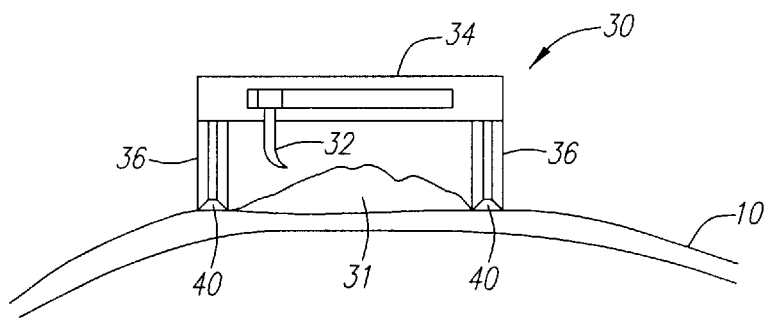
FIG. 2 is an elevational view illustrating a mechanical fat removal device for removing fat on the surface of a pericardium, according to an embodiment of the invention.

FIG. 2 shows a fat removal device 30 that may be introduced into a patient's body to remove fat 31 on the outer surface of the pericardium 10. The device 30 includes a fat removal member 32, such as a scraper, a blade, a grinder, and the like. The fat removal member 32 is supported by a housing 34 that rests on the surface of the pericardium 10. The housing 34 includes legs 36 that are adjustable by setting screws or dials (not shown) to vary a height and position of the fat removal member 32 relative to the surface of the pericardium 10. The legs 36 include vacuum ports 40 that may anchor the device 30 to the surface of the pericardium 10 by suction, and/or may pull the surface to tension it as a drum skin for more effective fat removal. The fat removal member 32 is movable to remove the fat 31. Fat removal may be performed progressively by gradually reducing the height of the fat removal member 32 until it reaches the surface of the pericardium 10.

Figure 3:
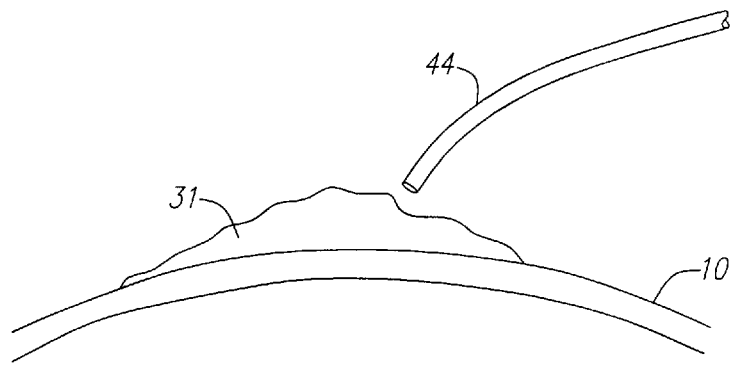
FIG. 3 is an elevational view illustrating a suction wand for removing fat on the surface of the pericardium, according to another embodiment.

Pericardial liposuction may be performed using a suction wand 44 as shown in FIG. 3. The wand 44 may be coupled to a vacuum source that is sufficiently strong for removing the fat 31 in a manner similar to cosmetic liposuction. The suction wand 44 may employ steerable controls to reach different parts of the pericardium 10 in a minimally invasive procedure. Pericardial liposuction may also be well suited for use in conjunction with a fat dissolving chemical compound for more effective fat removal.

Figure 4:
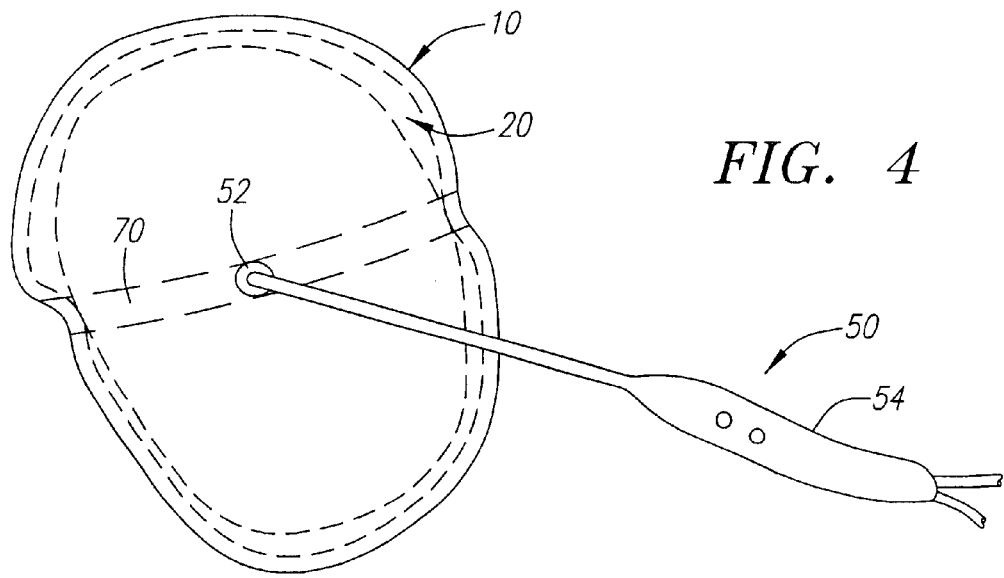
FIG. 4 is a perspective view of a radiofrequency device illustrating heating of the pericardium along a line according to an embodiment of the invention.
Figure 4A:
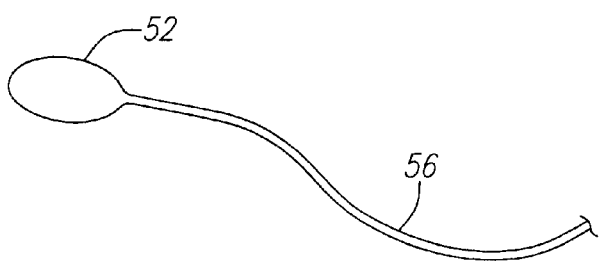
FIG. 4A is a perspective view of a radiofrequency device having a heating member connected to a catheter probe.

FIG. 4 shows a heating device 50 having a distal heating portion 52 placed in contact with, or in close proximity to, the external surface of the pericardium 10. The heating portion 52 may be supported on a handpiece or probe 54. Alternatively, the heating portion 52 may be introduced into the patient's body minimally invasively using a catheter shaft 56, as shown in FIG. 4A. The catheter shaft 56 may typically be inserted through a guide wire lumen that guides the distal heating portion 52 into the region of the heart adjacent the pericardium 10. Apparatus and techniques for negotiating a catheter through a patient, as well as internal exposure devices for presenting the target anatomy, are known in the art.

One preferred embodiment of the invention uses radiofrequency (RF) energy for heating. The distal portion 52 of an RF heating device includes an RF electrode (not shown) that is coupled to an RF generator provided outside of the patient's body (also not shown). The RF heating device may employ a monopolar system in which the distal portion of the heating device includes a single active electrode, and a passive electrode is attached to an outer body surface of the patient. The patient's body serves to complete the electrical circuit. Alternatively, the RF heating device may apply RF energy in a bipolar manner by providing both active and passive electrodes in the distal portion 52. The active and passive electrodes may be spaced apart from each other by a predetermined distance. The electrical circuit is completed by the body tissue disposed between the active and passive electrodes.

The RF heating device delivers a controlled amount of RF energy so that there is an effective transfer of thermal energy to the target region of the pericardium to alter the collagen-containing connective tissue without causing dissociation or breakdown of the collagen fibers. One way to ensure viability of the pericardial tissue is to use a temperature-controlled RF heating device that senses the temperature during treatment and may be dynamically controlled to adjust the RF energy supplied to the electrode. Temperature-controlled RF heating devices are commercially available, for example, from Oratec Intervention, Inc. of Menlo Park, Calif. For example, a temperature sensor, such as a thermocouple, thermister, and the like (not shown), may be provided on the distal portion 52, preferably on or adjacent to the electrode for providing feedback to the RF generator or other controller. Thus, the temperature may be monitored and the output of the RF generator adjusted to ensure that the treated tissue is altered without causing dissociation or breakdown of the collagen fibers or ablation of the tissue. For example, it may be desirable to heat the target tissue to a temperature of between about forty and ninety (40–90) degrees Celsius for between about twenty and one hundred twenty (20–120) seconds.

Figure 5:
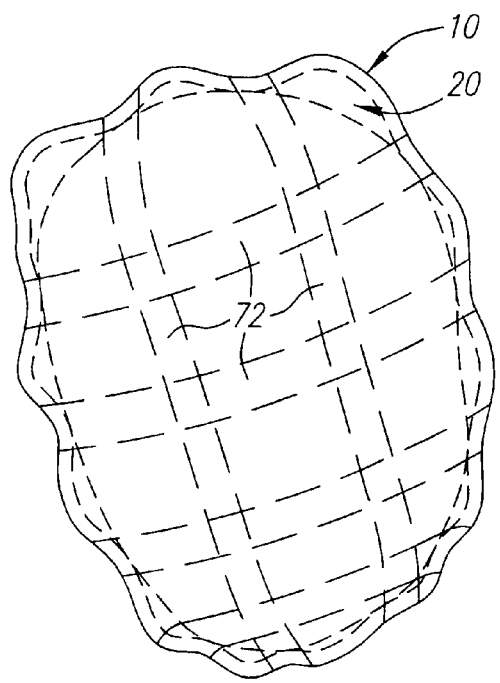
FIG. 5 is a perspective view of a pericardium that has been heated along spaced-apart lines in a grid.

In FIG. 4, the heating device 50 applies thermal energy along a band of treated pericardium 70. FIG. 5 shows a plurality of bands of treated pericardial tissue 72 that are spaced apart in a grid. Alternatively, the entire outer surface of the pericardium 10 may be subjected to heat treatment.

Figure 6:
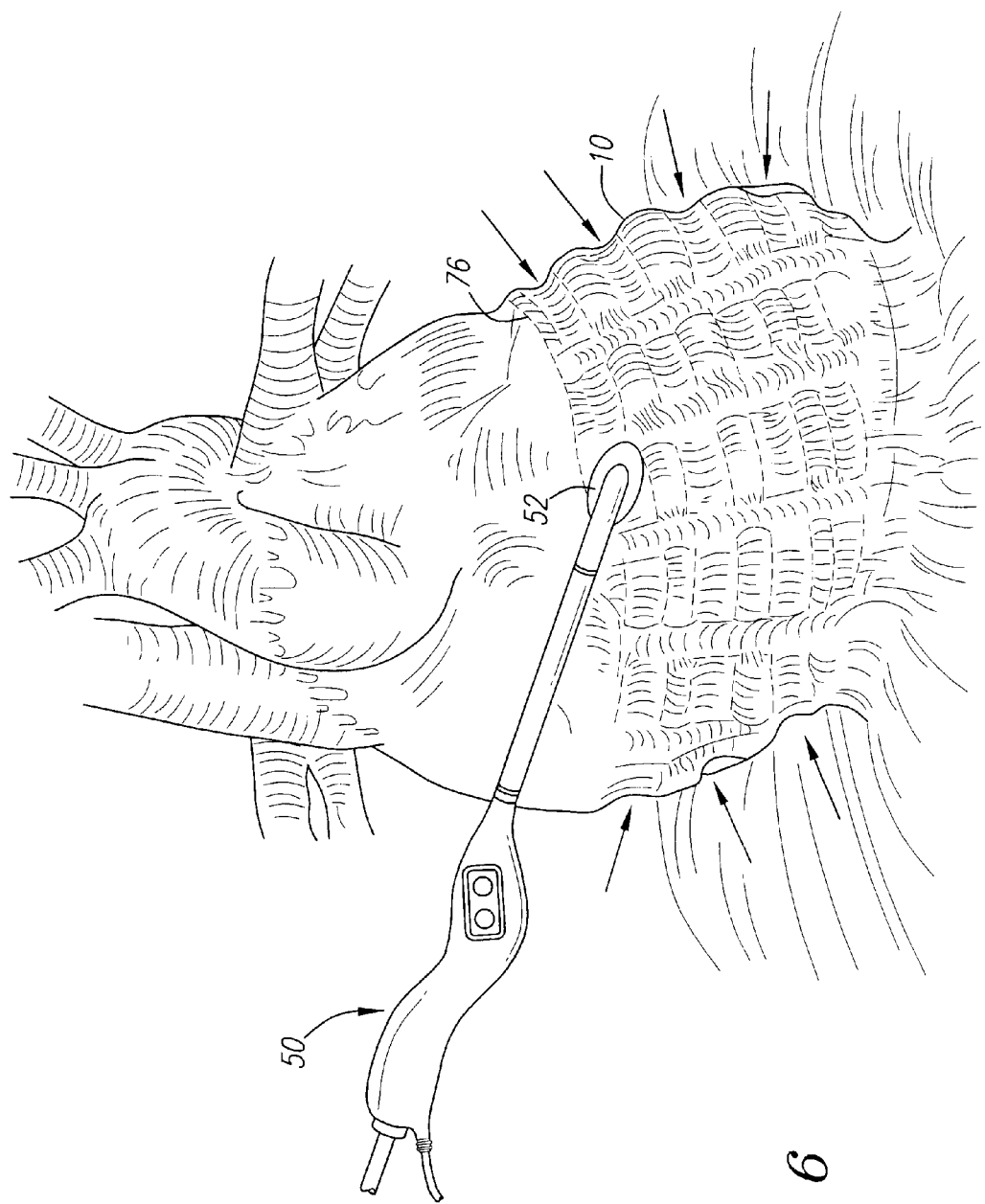
FIG. 6 is a perspective view of a heart, illustrating heating of the pericardium below the AV groove.

According to a specific embodiment, selective heating of the pericardium 10 takes place along the AV (atrio-ventricular) groove 76, which separates the left and right atria (LA, RA) from the ventricles, and extends down to the lower apex, as illustrated in FIG. 6. This causes local enhancement of the pericardium 10 to restrain specific chambers of the heart such as the left ventricle. Selective heating may be appropriate for treating patients suffering from or at risk of various forms of heart failure including ischemic, idiopathic, atrial fibrillation, or mitral valve induced heart failure.

Figure 7:
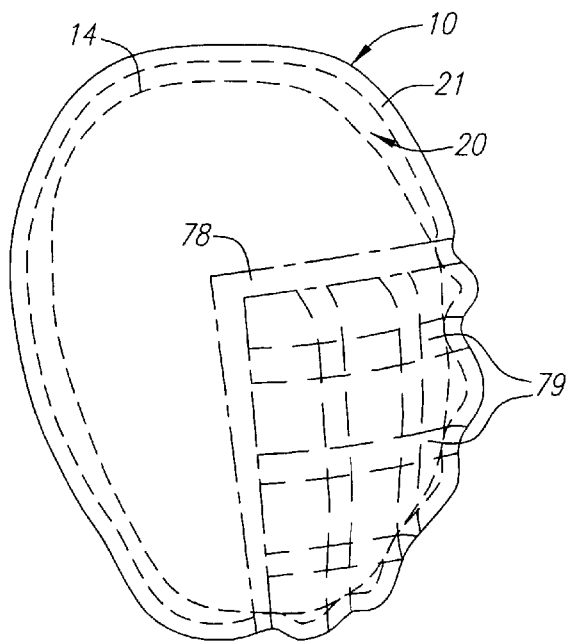
FIG. 7 is a perspective view of a pericardium, illustrating selective heating of the pericardium in a localized region.

Another way to localize thermal treatment is to anchor a portion of the pericardium to the myocardium to isolate a region of the pericardium, and then thermally treat the isolated region of the pericardium, as illustrated in FIG. 7. For example, a bioadhesive 78 may be applied between the pericardial sac 21 and the epicardium 14 by inserting an applicator through the pericardial sac 21 into the pericardial space 20. Alternatively, the pericardial sac 21 may be mechanically attached to the epicardium 14 or myocardium 16, e.g., by suturing or clipping. The pericardial sac 21 is typically anchored along a boundary of a region to be heat-treated, such as along the AV groove. The heat treatment produces a plurality of bands of treated pericardium 79 within the anchored boundary.

Anchoring the pericardial sac to the myocardium is desirable in cases where the pericardium is not suitable for treatment throughout its extent. For example, excess fat or prior surgery may render portions of the pericardium untreatable. The more viable portions are thus treated and used to form a fixing patch. After treatment, the suture material, clips, or other anchoring elements may be removed.

Figures 8, 9:
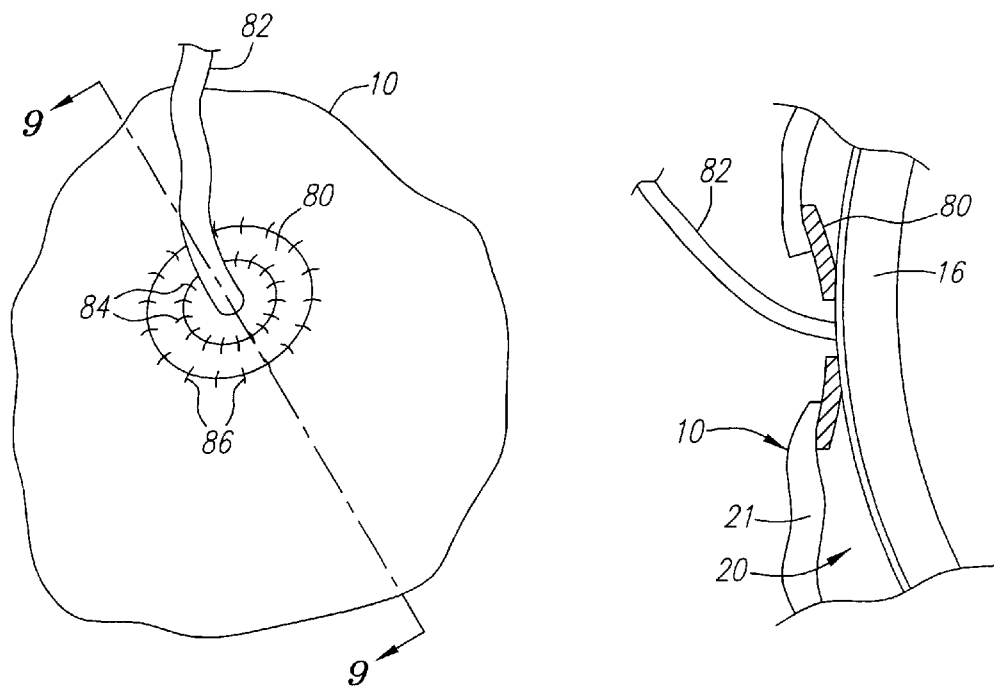
FIG. 8 is a front view of a pericardium, illustrating anchoring of a portion of the pericardium to the myocardium around an anastomosis.
FIG. 9 is a cross-sectional side view of the pericardium of FIG. 8, taken along line 9—9.

It may also be desirable to anchor a portion of the pericardial sac to the myocardium to provide strain relief, for example, for coronary artery bypass graft (CABG) sites. For patients who have had prior CABG grafts or who are undergoing a CABG procedure at the time of treatment for heart failure, it may be desirable to provide strain relief to the anastomosis site to prevent the anastomosis from coming apart or kinking. One way to do so is to anchor a ring of the pericardium to the myocardium around the anastomosis. Another way is to anchor a ring of biomedical material 80 that is physiologically inert into the myocardium 16 around the anastomosis of the CABG site 82, and attach the treated or untreated pericardium 10 to the ring of biomedical material 80, as illustrated in FIGS. 8 and 9. The biomedical material may be elastic or substantially inelastic, but desirably is sufficiently stiff to provide adequate constraint around the anastomosis as well as the myocardium 16. An example of a suitable biomedical material is a Dacron™ type material.

FIGS. 8 and 9 show a plurality of anchoring members 84 anchoring the ring of biomedical material 80 to the myocardium 16, and a plurality of attachment members 86 attaching the pericardium 10 to the ring 80. The anchoring members 84 and attachment members 86 may include suture material stitched by a suturing device, clips applied by a clip applier, staples, and the like.

The above treatment techniques may be performed from inside the pericardial space, as well as from outside the pericardium. When the pericardium is treated from inside the pericardial space, i.e., between the parietal sac and the epicardium, penetration of the fibrous pericardium and parietal sac may be performed by any method known in the art. Prior to penetrating the pericardial sac, it is preferable to pull the sac away from the epicardium to avoid accidental damage to the epicardium. Access to the pericardial space may typically be done minimally invasively.

FIG. 10 shows a heating device 90 penetrating through an incision 92 of the pericardial sac 21 into the pericardial space 20 for treating the inner surface of the pericardial sac 21. In sternotomy and thoracotomy cases, a device similar to the heating wand shown in FIG. 4 may be used. For smaller incisions, a malleable or steerable energy delivery wand is desirable. Alternatively, a heating device delivered by a catheter such as that shown in FIG. 4A may be employed.

Instead of RF energy, other ways of heating the pericardium may be used. By way of example, FIG. 11 shows a heating device 100 that uses a heated fluid, such as water, that is circulated via a circulation path 102 from a heater 104 to the distal heating portion 106 and back to the heater 104 by a pump 108. The distal heating portion 106 is typically made of a heat conducting material to facilitate heat transfer from the heated fluid to the pericardium, while the rest of the heating device 100 is typically made of a heat insulating material. The fluid heating device 100 may be temperature-controlled to achieve the desired heating of the pericardium.

The heating devices of FIGS. 4, 10, and 11 have probe-like structures with distal portions that are maneuvered around the pericardium to heat the tissue. Heating devices having other structures may also be used. For example, turning to FIG. 12A, a heating basket or umbrella 110 is shown that has a generally concave shape configured to fit around the external surface of the pericardium. The heating basket 110 may overlie substantially the outer surface of the entire pericardium, or only a portion of the pericardium such as the ventricles below the AV groove. The heating basket 110 includes a plurality of RF electrodes 112 facing the pericardium for delivering RF energy to multiple locations of the pericardium. The RF heating basket 110 may employ a temperature-controlled multipolar system. An example of a temperature-controlled multipolar RF system is found in U.S. Pat. No. 5,931,835, the disclosure of which is expressly incorporated herein by reference.

The heating basket 110 may be collapsible and may be delivered into a patient's body in a minimally invasive manner using a placement tool 116. The placement tool 116 includes a cannula sleeve 120 that may be advanced to enclose the collapsed heating basket 110. A guide wire 122 may be coupled to the basket 110, for example, at a lower region opposite the open end of the basket 110. The guide wire 122 may be directed into the cannula 120 until the basket 110 abuts the end of the cannula 120, whereupon further direction of the guide wire 122 through the cannula 120 collapses the basket 110 and pulls it into the cannula 120. Once the cannula 120 reaches the desired location near the pericardium, the guide wire 122 may be manipulated to guide the basket 110 out of the cannula 120 such that the basket wraps substantially around the pericardium. The basket 110 may be spring-loaded to open up automatically when it emerges from the cannula 120, or a mechanism may be used to open the basket and wrap it around the pericardium. After treatment, the basket 110 may be retrieved by pulling on the guide wire 122 to collapse the basket 11 as it is drawn back into the cannula 120, and then removing the cannula 120 from the patient's body.

FIG. 12B shows a heating basket 130 that is configured to be placed inside the pericardial space. The basket 130 includes a plurality of external electrodes 132 for heating the inner surface of the pericardial sac. The basket 130 may include a guide wire 138 and may be introduced into and retrieved from the pericardial space using a placement tool 134 including a cannula 136 that penetrates the pericardial sac, in a similar manner as that described for the basket of FIG. 12A.

Heated fluid may also be used in a basket configuration for heating the pericardium. FIG. 13 shows a heating basket 140 having a heated fluid circulation path 142 that winds throughout the outer surface of the basket 140 for heating the inner surface of the pericardial sac. The basket 140 may be connected to a source of heated fluid (not shown) via tube 149 that communicates with the circulation path 142. The heating basket 140 may include a guide wire 148, and may be deployed and retrieved using a placement tool 144 including a cannula 146 in a manner similar to that described for the basket of FIG. 12A.

Instead of or in addition to heat, a chemical may be used to treat and enhance the pericardium. For example, a chemical that causes stiffening or crosslinking of collagen fibers may be applied to the pericardium to cause stiffening, strengthening, tightening, reshaping, and/or shrinking of the pericardium to enhance the restraining and supporting capability of the pericardium around the heart. An example of a chemical that may be used is glutaraldehyde, which has been used to treat pericardial valves in valve replacement procedures. A nontoxic chemical is generally preferred so that it may be applied both to the external surface of the pericardium and from within the pericardial space.

Figure 14:
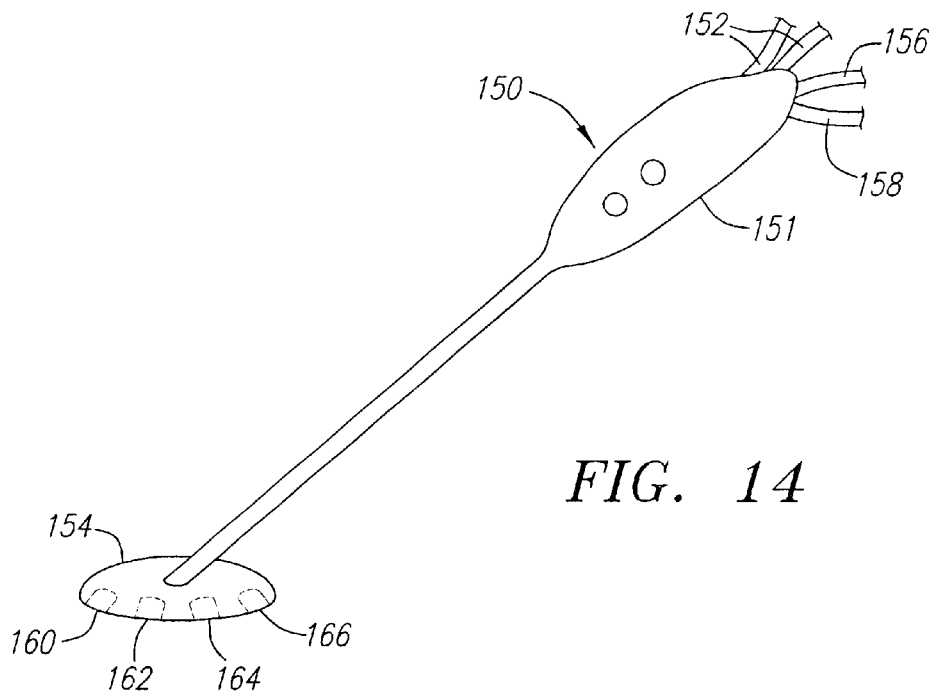
FIG. 14 is a perspective view of a heating device having radiofrequency electrodes for heating a pericardium and fluid flow ports for introducing a chemical for treating the pericardium.

FIG. 14 shows a device 150 for delivering both radio frequency (RF) energy and a chemical to treat the pericardium thermally and/or chemically. RF lines 152, such as wires or other conductors, extend between proximal and distal portions 151, 154 of the device 150. The RF lines 152 may be coupled to an RF generator for supplying RF energy to the distal portion 154. The distal portion 154 includes an active electrode 160 and a passive electrode 162 coupled to the RF lines and forming a bipolar system.

The device 150 also may include a chemical delivery line 156, connectable to a source of chemical, such as a pump, for introducing a chemical to the distal portion 154, and a vacuum line 158, connectable to a source of vacuum, for withdrawing the chemical. The distal portion 154 further includes a chemical inflow port 164 communicating with the delivery line 156 for introducing the chemical, and a vacuum port 166 communicating with the vacuum line 158 for removing the chemical from the treatment site. Contemporaneous removal the chemical as it is introduced may be particularly advantageous for chemicals that are toxic. Alternatively, instead of suction, removal of the chemical may be done using a sponge element and the like, which may be disposed on the distal portion 154.

Other ways of introducing the chemical to the pericardium may be used. For example, a delivery tube may be guided into the pericardial space by a catheter for delivering the chemical into the space, and a vacuum tube may be placed at another location of the pericardium for removing the chemical.

Figure 15:
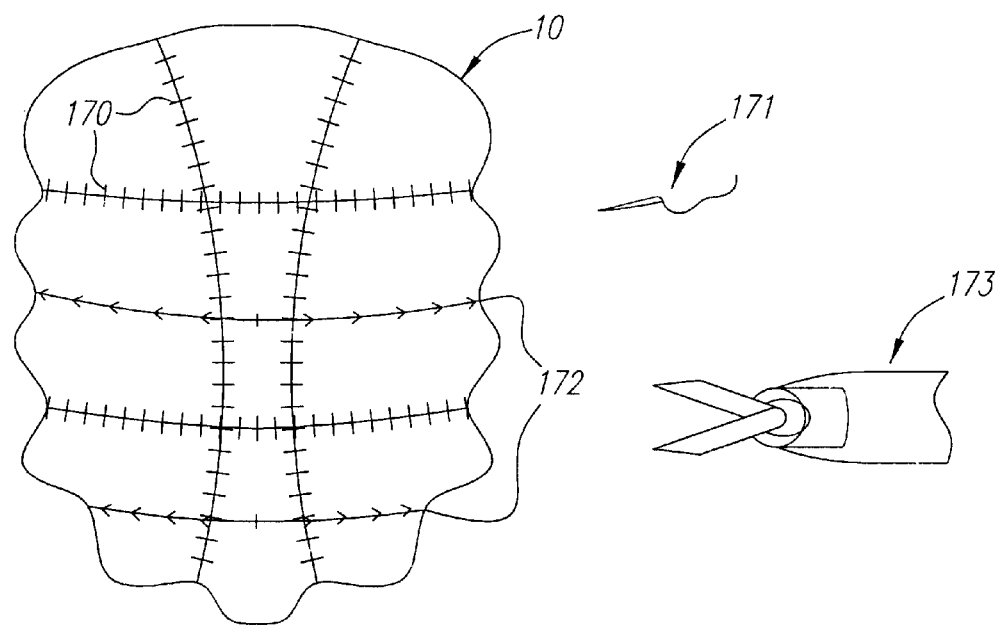
FIG. 15 is a perspective view of a pericardium treated by placation.

Plication may also be used instead of or in addition to the above-described treatments to strengthen, shorten, tighten, reshape, and/or stiffen the pericardium. Plication of the pericardium typically involves plicating portions of the pericardial sac using plicating members to reduce the compliance and/or modify the shape of the pericardium. Suitable placation members include suture materials, clips, and the like. FIG. 15 shows placation of the pericardium by suturing with a suture material 170 using a suturing device 171 and application of clips 172 using a clip applier 173.

The above procedures may be performed on a stopped heart or a beating heart. The treated pericardium may help increase the ejection fraction in patients with dilated or nondilated heart failure. The pericardium may do so by restricting the outward motion of the myocardium and force more contraction towards the center of the left ventricle, thereby increasing the ejection fraction. As a result, the benefits of the Batista procedure, a left ventricle wall resection surgical procedure, may be realized without the need to remove large pieces of the heart.

Figure 16:
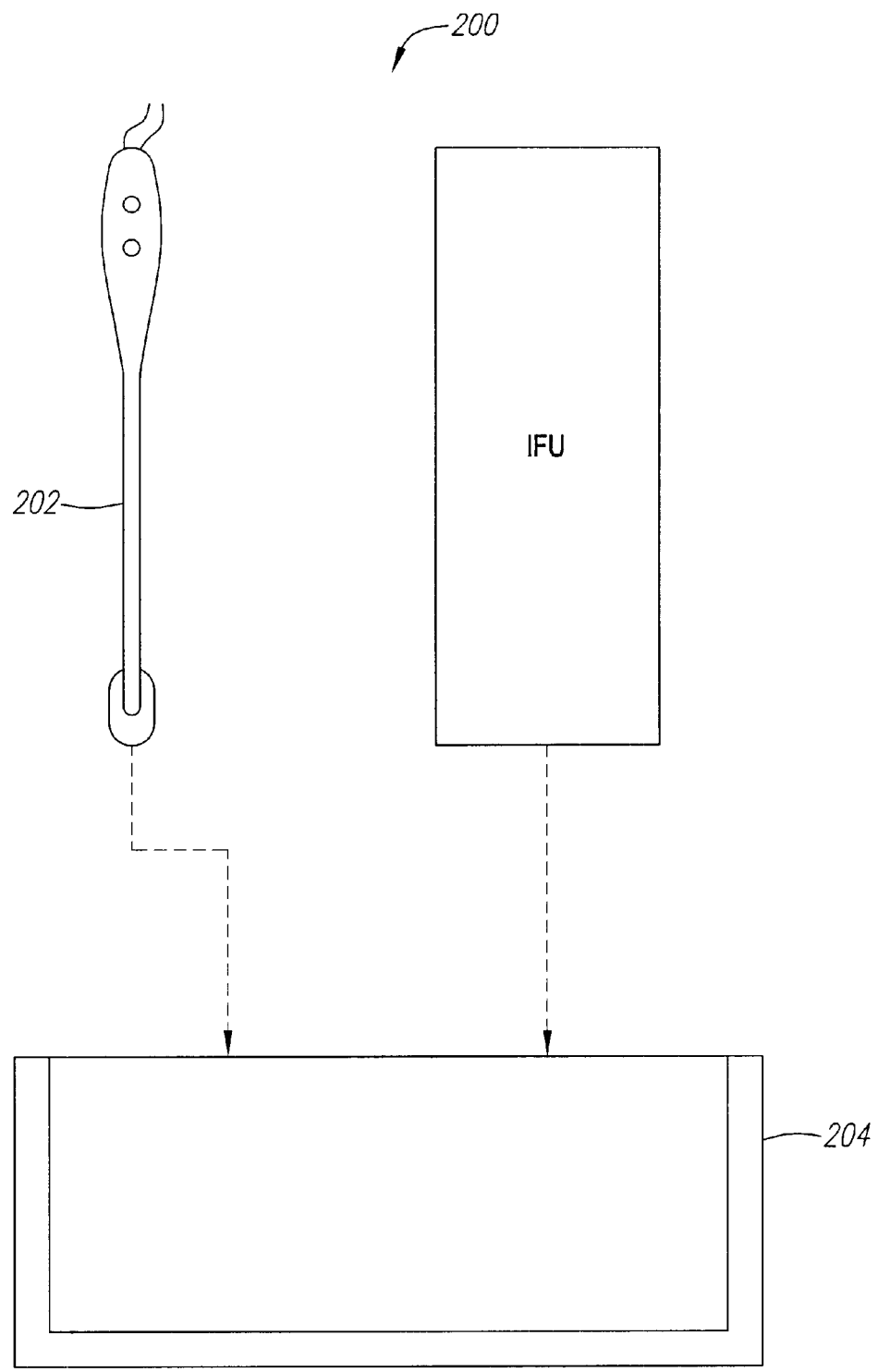
FIG. 16 illustrates a kit constructed in accordance with the principles of the present invention.

In FIG. 16, a kit 200 according to the present invention includes at least a member for modifying the pericardium 202 and instructions for use (IFU) setting forth a method according to the present invention for modifying the pericardium. For illustrative purposes, the member 202 in FIG. 16 has a probe-like configuration. The member 202, however, may include one or more of the devices described above, such as the heating devices of FIGS. 4–13, the fluid delivery device of FIG. 14, and/or the plicating devices of FIG. 15. Optionally, the kit 200 may further include a device for accessing the pericardium, as well as packaging 204, typically in the form of a box, pouch, tray, tube, and the like. Instructions for use will usually be printed on a separate sheet of paper in the form of a package insert, but may also be printed partly or wholly on the packaging itself.

The above-described arrangements of apparatus and methods are merely illustrative of applications of the principles of this invention and many other embodiments and modifications may be made without departing from the spirit and scope of the invention as defined in the claims. The scope of the invention should, therefore, be determined, not with reference to the above description, but instead should be determined with reference to the appended claims along with their full scope of equivalents.

All patents, applications, and publications referred to above are incorporated herein by reference in their entirety.

What is claimed is:

1. A method for treating a patient to inhibit remodeling of the heart, the method comprising modifying pericardial tissue within the heart's pericardium under conditions to inhibit remodeling of the heart.

2. A method as in claim 1, wherein the modifying step comprises heating at least a portion of the pericardium.

3. A method as in claim 2, wherein the pericardium is heated under conditions that shrink collagen within the pericardial tissue while retaining tissue viability.

4. A method as in claim 2, wherein the heating step comprises contacting the pericardial tissue with a probe that applies radio frequency energy to the pericardial tissue.

5. A method as in claim 4, wherein the probe is placed in contact with pericardial tissue on an outer surface of the pericardium.

6. A method as in claim 5, further comprising removing fat on the outside of the pericardium.

7. A method as in claim 6, wherein the step of removing fat comprises at least one of mechanically abrading the fat, thermally ablating the fat, applying a fat-dissolving chemical to the fat, or applying a suction to the fat.

8. A method as in claim 4, wherein the probe is placed in contact with the pericardial tissue from within a pericardial space of the heart.

9. A method as in claim 2, wherein the heating step comprises placing a heating element in contact with or in close proximity to the pericardial tissue and circulating a heated fluid through the heating element.

10. A method as in claim 2, wherein the pericardium is heated in a pattern of spaced-apart lines.

11. A method as in claim 10, wherein the spaced-apart lines are in a grid.

12. A method as in claim 2, wherein the entire pericardium is heated.

13. A method as in claim 2, wherein the pericardium is heated selectively below an AV groove of the heart.

14. A method as in claim 2, where the pericardium is heated selectively in a region overlying at least one of the ventricles.

15. A method as in claim 1, further comprising accessing a region of the pericardium.

16. A method as in claim 15, wherein the step of accessing the pericardium comprises at least one of surgically opening a patient's chest, forming an intercostal incision, or forming a subxiphoid access channel.

17. A method as in claim 15, wherein the pericardium is accessed transvascularly via the venous system.

18. A method as in claim 1, wherein the modifying step comprises applying a chemical to the pericardial tissue to reduce compliance of the pericardium.

19. A method as in claim 18, further comprising removing the chemical from the patient.

20. A method as in claim 19, wherein the chemical is removed substantially contemporaneously with applying the chemical.

21. A method as in claim 18, wherein the chemical includes glutaraldehyde.

22. A method as in claim 1, wherein the modifying step comprises plicating the pericardium.

23. A method as in claim 22, wherein the plicating step comprises suturing or clipping the pericardium.

24. A method as in claim 1, further comprising stopping the heart while modifying the pericardium.

25. A method as in claim 1, wherein the heart remains beating while modifying the pericardium.

26. A method as in claim 1, further comprising isolating a target region of the pericardium to be modified.

27. A method as in claim 26, wherein the isolating step comprises anchoring a portion of the pericardium surrounding the target region to the myocardium.

28. A method as in claim 27, wherein the anchoring step comprises suturing or clipping the portion of the pericardium surrounding the target region to the myocardium.

29. A method as in claim 27, wherein the anchoring step comprises coupling a ring of the pericardium with the myocardium around an anastomosis.

30. A method as in claim 29, wherein the step of coupling a ring comprises attaching the ring of pericardium to an annular piece of biomedical material and attaching the annular piece of biomedical material to the myocardium around the anastomosis.

31. A method for treating patients suffering from or at risk of heart failure, the method comprising:

providing a device having a heating member;

placing the heating member in contact with or in close proximity to a pericardium of the heart; and supplying energy to the heating member to cause heating of the pericardium under conditions and for a time selected to reduce or eliminate remodeling of the heart.

32. A method as in claim 31, wherein the heating member includes an electrode and supplying energy to the heating member comprises applying radiofrequency energy through the electrode to the pericardium.

33. A method as in claim 31, wherein the heating member includes a circulation path and supplying energy to the heating member comprises circulating a heated fluid through the circulation path of the heating member.

34. A method as in claim 31, wherein the heating member is placed in contact with or in close proximity to an outside surface of the pericardium.

35. A method as in claim 31, wherein the heating member is placed in contact with or in close proximity to an inside surface of the pericardial sac of the pericardium.

36. A method as in claim 31, wherein the device includes a fluid delivery port and the method further comprises introducing a chemical through the fluid delivery port to the pericardium to reduce compliance of the pericardium.

37. A method as in claim 36, wherein the device includes a suction port and the method further comprises withdrawing through the suction port the chemical introduced to the pericardium.

38. In a method for treating patients suffering from or at risk of heart failure, of the type involving provision of constraint around the heart wherein constraining forces of a pericardium around the heart are inadequate to prevent remodeling of the heart, the improvement comprising modifying pericardial tissue of the pericardium in a manner sufficient to inhibit remodeling of the heart while retaining viability of the heart.

39. A method as in claim 38, wherein the modifying step comprises introducing a stiffening chemical to stiffen the pericardium.

40. A method as in claim 38, wherein the modifying step comprises shrinking at least a portion of the pericardium.

41. A method as in claim 40, wherein the shrinking step comprises applying thermal energy to the pericardium under conditions that shrink collagen within the pericardial tissue while retaining tissue viability.

42. A method as in claim 40, wherein the shrinking step comprises tensioning the pericardium to restrain the heart.

43. A device for treating a pericardium of a heart, the device comprising:

a heating member configured to be placed in contact with or in close proximity to the pericardium, the heating member including a fluid delivery port;

a source of energy coupled with the heating member for providing energy to the heating member to cause heating;

a fluid delivery line extending from the fluid delivery port;

a source of chemical communicating with the fluid delivery line for introducing the chemical through the fluid delivery port to the pericardium, the chemical being configured for stiffening the pericardium.

44. The device of claim 43, further comprising a suction line extending from a suction port, and a vacuum source communicating with the suction line for withdrawing through the suction port the chemical introduced to the pericardium.

45. The device of claim 43, wherein the heating member includes a passive electrode spaced from an active electrode, and wherein the source of energy comprises a radiofrequency source for providing radiofrequency energy through the electrodes to the pericardium.

* * * * *